United States Patent [19]

Uwajima et al.

[11] Patent Number: 4,710,470
[45] Date of Patent: Dec. 1, 1987

[54] PROCESS FOR PRODUCING NEURAMINIDASE

[75] Inventors: Takayuki Uwajima; Kazuo Aisaka, both of Machida, Japan

[73] Assignee: Kyowa Hakko Kogyo Co., Ltd., Tokyo, Japan

[21] Appl. No.: 636,552

[22] Filed: Aug. 1, 1984

[30] Foreign Application Priority Data

Aug. 4, 1983 [JP] Japan .................................. 58-142803

[51] Int. Cl.$^4$ .......................... C12N 9/24; C12Q 1/00; C12Q 1/34; C12Q 1/26; C12Q 1/28; C12R 1/29; C12R 1/30
[52] U.S. Cl. ........................................ 435/200; 435/4; 435/18; 435/25; 435/28; 435/867; 435/868
[58] Field of Search ................ 435/4, 28, 18, 25, 867, 435/868, 195, 810, 200, 26

[56] References Cited

U.S. PATENT DOCUMENTS

| | | | |
|---|---|---|---|
| 3,991,183 | 11/1976 | Celmer et al. | 424/118 |
| 4,071,408 | 1/1978 | Flashner et al. | 195/62 |
| 4,246,342 | 1/1981 | Misaki et al. | 435/25 |
| 4,316,954 | 2/1982 | Snoke et al. | 435/4 |
| 4,416,982 | 11/1983 | Tsuda et al. | 435/11 |

FOREIGN PATENT DOCUMENTS

| | | | |
|---|---|---|---|
| 0038529 | 10/1981 | European Pat. Off. | 12/11 |
| 1061095 | 3/1967 | United Kingdom | 12/1 |

OTHER PUBLICATIONS

ATCC Catalogue of Strains I, 15th ed. (1982) 144:5.
Bergey's Manual of Determinative Bacteriology, 8th Ed. (1974) 848,852:3.
Biochim. Biophys. Acta., vol. 523 (1978) 435:42.
Metabolite, 16 (5), 761 (1979).
Biochem. Biophys. Acta, 350, 425-431 (1974).
J. Biochem., 82, 1425-1433 (1977).
J. Bacteriol., 119 (2), 394-400 (1974).
Canadian J. Microbiology 18, 1007 (1972).

*Primary Examiner*—Esther M. Kepplinger
*Attorney, Agent, or Firm*—Fitzpatrick, Cella, Harper & Scinto

[57] ABSTRACT

Neuraminidase is produced by culturing a neuraminidase producing microorganism belonging to the genus Micromonospora. The neuraminidase is useful for the quantitative determination of a sialic acid-containing substance in a sample.

4 Claims, No Drawings

PROCESS FOR PRODUCING NEURAMINIDASE

BACKGROUND OF THE INVENTION

The present invention relates to a process for producing neuraminidase and a method and a reagent, for the determination of a sialic acid-containing substance. More particularly, the present invention relates to a process for producing neuraminidase by culturing a microorganism belonging to the genus Micromonospora and a method and a reagent for the quantitative determination of a sialic acid-containing substance utilizing such neuraminidase.

Neuraminidase (EC 3.2.1.18) is a hydrolase which acts to liberate the sialic acid residue using, as a substrate, the ketoside having an α-configuration of a sialic acid (collective name of an acyl derivative of neuraminic acid) located at the terminal of sugar proteins, sugar lipids and the like which are important constituents of the living body.

It is known that neuraminidase is widely distributed in microorganisms such as virus, bacteria and actinomyces, and tissues of birds, mammals, etc. It is also known that neuraminidase can be used for the quantitative assay of sialic acid-containing substances in the living body such as serum.

Heretofore, neuraminidase has been obtained by culturing a neuraminidase producing microorganism in a culture vessel to which colominic acid, and a leaching liquid or extracts from various animal tissues are added as neuraminidase-inducing materials. [METABOLITE, 16 (5), 761 (1979), Biochim. Biophys. Acta, 350, 425–431 (1974), J. Biochem. 82, 1425–1433 (1977), J. Bacteriol. 119 (2), 394–400 (1974), Canadian J. Microbiology 18, 1007 (1972), Japanese Published Examined Patent Application No. 11991/75]. Such methods, however, suffer in that it is extremely difficult from an economical viewpoint to obtain and use these neuraminidase-inducing materials in large quantities. Accordingly, the known methods for producing neuraminidase are not economically feasible on a commercial scale and a process for industrially producing neuraminidase at low cost is in demand.

To this end, the present inventors have found that when microorganisms belonging to the genus Micromonospora are cultured in a culture medium, neuraminidase is produced in marked quantities in the culture liquor and can be readily recovered therefrom. It has also been found that the neuraminidase so produced is useful in a method and as a reagent for the quantitative determination of sialic acid-containing substances.

SUMMARY OF THE INVENTION

According to the present invention, neuraminidase is produced by culturing a microorganism belonging to the genus Micromonospora which is capable of producing neuraminidase in a culture medium, accumulating neuraminidase in the culture liquor and then recovering the enzyme therefrom.

In accordance with another aspect of the invention, a method is provided for the quantitative determination of a sialic acid-containing substance in a sample which comprises decomposing the sialic-acid containing substance in the sample with neuraminidase derived from a microorganism belonging to the genus Micromonospora to form N-acetylneuraminic acid; decomposing the N-acetylneuraminic acid with N-acetylneuraminic acid lyase (NANA lyase) to form pyruvic acid and thereafter either reacting the pyruvic acid with NADH in the presence of lactic acid dehydrogenase and determining the reduction of the amount of NADH or reacting the pyruvic acid with pyruvate oxidase in the presence of peroxidase, thiamine pyrophosphate, 4-aminoantipyrine, phenol and a magnesium salt and colorimetrically determining the degree of pigment formation.

In accordance with the composition of matter aspect of the invention, reagents are provided for the quantitative determination of a sialic acid-containing substance in a sample which comprise neuraminidase derived from a microorganism belonging to the genus Micromonospora, N-acetylneuraminic acid lyase and either NADH and lactic acid dehydrogenase or pyruvate oxidase, peroxidase, thiamine pyrophosphate, a magnesium salt, 4-aminoantipyrine and phenol.

DESCRIPTION OF INVENTION

The microorganism to be used in the present invention for the production of neuraminidase is any strain as long as it belongs to the genus Micromonospora and is capable of producing neuraminidase. Examples of preferred strains are *Micromonospora viridifaciens* ATCC 31146, *Micromonospora globosa* NRRL B-2673 and *Micromonospora chalcea* ATCC 12452. The strains ATCC 31146 and ATCC 12452 are deposited with the American Type Culture Collection and are available to the public therefrom. The strain NRRL B-2673 is deposited with ARS Culture Collection Reserch Fermentation Laboratory in the general collection and is also freely available.

The bacteriological properties of the species to which the foregoing preferred strains belong are described in the following publications:

U.S. Pat. No. 3,991,183 (1977) "*Micromonospora viridifaciens*"

"Bergey's Manual of Determinative Bacteriology", 8th ed., (1974) "*Micromonospora globosa*", page 852, "*Micromonospora chalcea*", page 848

For culturing the microorganisms according to the invention, either a natural medium or a synthetic medium may be used as long as it contains suitable carbon sources, nitrogen sources, inorganic materials and other nutrients.

As carbon sources, various carbohydrates such as glucose, fructose, sucrose, maltose, mannose, starch, starch hydrolyzate, molasses; various sugar alcohols such as glycerol, sorbitol and mannitol; various organic acids such as acetic acid, lactic acid, pyruvic acid, fumaric acid and citric acid; various alcohols such as methanol and ethanol; various glycols such as ethylene glycol and propylene glycol; various amino acids or hydrocarbons such as n-hexadecane, leaching liquid from bovine heart or bovine brain, bovine blood powder and the like may be used.

As nitrogen sources, ammonia or various inorganic and organic ammonium salts such as ammonium chloride, ammonium carbonate, ammonium phosphate, ammonium nitrate and ammonium acetate; urea, amino acids and other nitrogen compounds; as well as nitrogen-containing organic materials such as peptone, NZ-amine, meat extract, corn steep liquor, casein hydrolyzate, chrysalis hydrolyzate, fish meal or its digested matter, defatted soybean or its digested matter and the like may be used.

As inorganic materials, potassium dihydrogen phosphate, dipotassium hydrogen phosphate, potassium chloride, magnesium sulfate, manganese sulfate, ferrous sulfate, sodium chloride, calcium carbonate, etc. may be used.

The addition of sialic acid-containing substances such as colominic acid and mucin to the culture medium generally results in the production of neuraminidase in larger quantities. In such case, the amount of these additives ranging from 0.01 to 1.0% (W/V) per weight of the medium can give good results.

Culturing is carried out by aeration-agitation at a pH of from 6.0 to 7.0 and at a temperature of from 25° to 35° C. for 4 to 5 days. Under these conditions, a considerable amount of neuraminidase is produced and accumulated in the culture broth, and mainly in the culture liquor.

After completion of culturing, the culture liquor is filtered or subjected to centrifugal separation to remove the microbial cells and obtain a filtrate or supernatant. The filtrate or supernatant is then treated in conventional manner for the separation and purification of enzymes, e.g., salting-out, precipitation with organic solvents, dialysis, ion exchange column chromatography, gel filtration, freeze drying, etc. to recover purified neuraminidase.

As an example, the culture filtrate is subjected to salting-out with ammonium sulfate of 90% saturation. The precipitates formed are dissolved in a buffer solution, and subjected to dialysis. The solution is absorbed onto a column filled with an anion exchange resin such as DEAE-Sephadex and DEAE-cellulose. The adsorbed enzyme is eluted out by concentration gradient of sodium chloride or ammonium sulfate. The enzyme eluted out is then purified by gel filtration with Sephadex G-75 or Bio Gel P-100.

The properties of the enzyme obtained in accordance with the present invention are described below using neuraminidase produced from *Micromonospora viridifaciens* ATCC 31146. Neuraminidase produced from *Micromonospora globosa* NRRL B-2673 and *Micromonospora chalcea* ATCC 12452 has the same essential properties.

Enzymatic activity of neuraminidase is calculated by reacting N-acetylneuraminic acid formed by the enzymatic reaction of neuraminidase and a substrate with N-acetylneuraminic acid lyase (EC 4.1.3.3), reacting the formed pyruvic acid with NADH in the presence of lactic acid dehydrogenase (EC 1.1.1.27) and measuring the reduction of absorbency of NADH at 340 nm with a spectrophotometer as compared to a blank.

The reaction is illustrated by the following equations (1), (2) and (3).

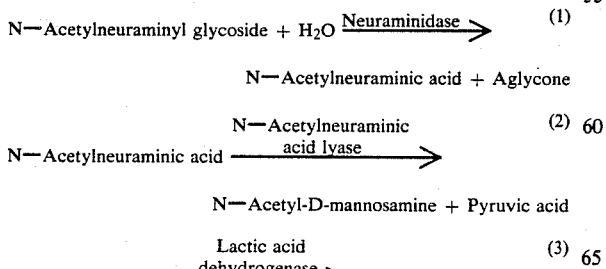

(a) Reagents:

| | | |
|---|---|---|
| (1) Substrate: 40 mg/ml colominic acid aqueous solution | | 0.1 ml |
| (2) Buffer: 200 mM citrate-sodium dihydrogen phosphate buffer (pH 5.0) | | 0.1 ml |
| (3) N—Acetylneuraminic acid lyase solution: Prepared so as to be 1 unit/ml using 10 mM phosphate buffer (pH 7.0) | | 0.05 ml |
| (4) NADH: 100 mM phosphate buffer Prepared so as to be 0.3 mM using the buffer (pH 7.4) | | 2 ml |
| (5) Lactic acid dehydrogenase: Prepared so as to be 300 units/ml using 100 mM phosphate buffer (pH 7.4) | | 0.01 ml |
| (6) Enzyme Solution | | 0.1 ml |

(b) Procedure

Reagents (1) and (2) were placed in a test tube and preheated at 37° C. for 5 minutes. Then, Enzyme solution (6) was added until the total amount of the solution is 0.5 ml followed by reaction with shaking at 37° C. for 15 minutes. The reaction was discontinued by heat treatment at 100° C. for 3 minutes. Then, reagent (3) was added and allowed to react at 70° C. for 15 minutes. Regent (4) was then added, and immediately thereafter, the absorbency at 340 nm ($OD_0min$) was measured. Reagent (5) was added and the mixture was reacted at 25° C. for 10 minutes. The absorbency at 340 nm ($OD_{10min}$) was measured and the difference $\Delta OD_{test}$ was determined. On the other hand, a change in absorbency $\Delta OD_{blank}$ was determined by performing the same procedure as described above using water in place of the enzyme as a control.

(c) Calculation of Potency 1 unit of neuraminidase is defined as the amount of enzyme for forming 1 μmole of N-acetylneuraminic acid at 37° C. for 1 minute. The absorptivity of 1 mM of NADH is reported to be 6.22 (The Merck Index, 9th Ed., page 824).

Accordingly, potency (A) to be calculated per 1 ml of an enzyme solution is determined by:

$$A = \frac{(\Delta OD_{test} - \Delta OD_{blank}) \times 2.55}{6.22 \times 0.10 \times 15}$$

$$= (\Delta OD_{test} - \Delta OD_{blank}) \times 0.273 (\text{unit/ml})$$

Neuraminidase obtained in the present invention is characterized by the following properties.

(1) Action

Catalyzes the reaction of liberating N-acetylneuraminic acid residue utilizing as a substrate the ketoside having α-configuration of N-acetylneuraminic acid located at the terminal of cyalo sugar complex.

(2) Substrate Specificity

Decomposes various N-acetylneuraminic acid ketosides such as colominic acid, N-acetylneuraminic acid lactose, fetuin and mucin.

| Substrate | Binding Mode | Relative Activity (%) |
|---|---|---|
| Colominic acid | α, 2-8 | 100 |
| N—Acetylneuraminic acid lactose | α, 2-3 (2-6) | 80.4 |
| Fetuin | α, 2-3 | 81.0 |
| Mucin | α, 2-6 | 203 |

Km value to N-acetylneuraminic acid lactose was approximately 2 mM.

(3) Optimum pH

The optimum pH is in the vicinity of 5.0 to 5.5 in a reaction at 37° C. for 15 minutes.

(4) Stable pH Range

The stable pH region is from 6.0 to 9.0 in a treatment at 4° C. for 20 hours.

(5) Range of Optimum Temperature for Activity

The optimum temperature is in the vicinity of 50° to 60° C. in a reaction at pH 5.0 for 15 minutes.

(6) Temperature Stability

The enzyme is stable up to 50° C. in a treatment at pH 6.0 for 15 minutes and is inactivated by about 50% at 55° C.

(7) Inhibition

The enzyme is inhibited by the following substances when reacted at 37° C. at pH 5.0.

| Inhibitor | Concentration (M) | Inhibition Rate (%) |
|---|---|---|
| N—Bromosuccinimide | $10^{-4}$ | 89.7 |
| " | $10^{-3}$ | 100 |
| PCMB* | $10^{-4}$ | 0.6 |
| " | $10^{-3}$ | 99.2 |
| TNBS** | $10^{-3}$ | 30.4 |

*PCMB = p-chloromercury benzoate
**TNBS = trinitrobenzenesulfonic acid (8) Molecular Weight Calculated to be about 30,000 by gell filtration using Sephadex G-150.

(9) Crystalline structure and elemental analysis were not determined because this enzyme was not crystallized.

(10) With this enzyme a single band was obtained by disc electrophoresis. Namely, migration was performed for about 90 minutes in a tris-glycine buffer (pH 8.3) using 7.5% polyacrylamide gel. By dyeing the gel with an amide black dyeing solution, a single protein band was observed.

The method for determination of a sialic acid-containing substance using neuraminidase according to the present invention is schematically represented as follows.

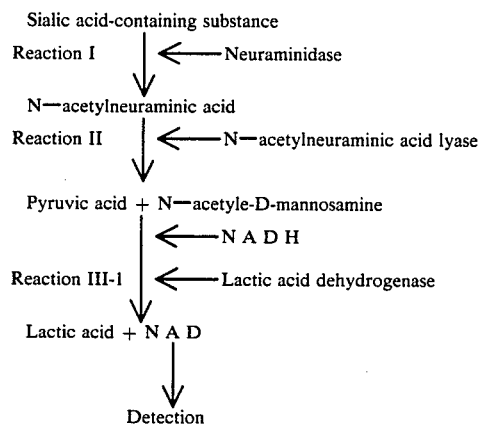

The foregoing reactions are generally carried out as follows:

Reaction I

A sialic acid-containing substance and neuraminidase are added to buffer solution (pH 6-8), and the reaction is usually carried out at 25° to 35° C. for 10 to 30 minutes.

As the sialic acid-containing substance, mucin, fetuin, immunoglobulin, erythrocyte, serum and ganglioside are exemplary.

Neuraminidase is used in an amount of 0.5 to 2.0 U. As the buffer solution, phosphate buffer solution, citrate buffer solution and the like may be used.

Reaction II

After the enzymatic reaction, 1 to 10 U of N-acetylneuraminic acid lyase (NANA lyase) is added to the reaction mixture. This reaction is usually carried out at 25° to 37° C. for 10 to 20 minutes.

Reaction III-1

NADH is then added to the reaction mixture to a final concentration of 0.24 mM. The absorbency of the solution is measured at 340 nm, and the value is expressed as $A_1$. Next, 10μl of lactic acid dehydrogenase is added to the mixture, and reaction is carried out at 25° to 37° C. for 5 to 10 minutes. The absorbency of the solution is again measured at 340 nm and the value is expressed as $A_2$.

The amount of sialic acid-containing substance is calculated from the value of $A_1-A_2$.

Instead of Reaction III-1, determination of a sialic acid-containing substance may be carried out by the following alternate Reaction III-2.

Reaction III-2

To the reaction mixture of Reaction II, 5–10 U of pyruvate oxidase, 50–100 U of peroxidase, 1 mg of thiamine pyrophosphate, 2 mg of $MgSO_4.7H_2O$, 1 mg of 4-aminoantipyrine and 1 mg of phenol are added, and the reaction is carried out at 25° to 37° C. for 5 to 10 minutes. The absorbency of the solution is measured at 500 nm and the amount of sialic acid-containing substance is calculated from a calibration curve.

The present invention also provides a reagent for determining a substrate for neuraminidase. The reagent comprises (A) 0.5 to 2.0 U of neuraminidase derived from a microorganism belonging to the genus Micromonospora, (B) 1 to 10 U of N-acetylneuraminic acid lyase, and either (C) a mixture of 0.3 to 0.9 μmole of NADH and 2 to 5 U of lactic acid dehydrogenase or (C') a mixture of 5 to 10 U of pyruvate oxidase, 50 to 100 U of peroxidase, 1 to 5 mg of thiamine pyrophosphate, 1 to 5 mg of a magnesium salt such as $MgSO_4.7H_2O$ and $MgCl_2.6H_2O$, 1 to 5 mg of 4-aminoantipyrine and 1 to 5 mg of phenol.

Certain specific embodiments of the invention are illustrated by the following representative examples.

EXAMPLE 1

In this example, *Micromonospora viridifacience* ATCC 31146 was inoculated into 300 ml of a medium (pH 7.0) comprising 1 g/dl glucose, 1 g/dl soluble starch, 0.75 g/dl peptone, 0.75 g/dl meat extract, 0.30 g/dl sodium chloride, 0.10 g/dl magnesium sulfate, 0.10 g/dl potassium dihydrogen phosphate and 0.1 g/dl colominic acid in a 2 l-Erlenmeyer flask and cultured with shaking at 30° C. for 48 hours.

Then, 600 ml of the culture liquor was transferred to a 30 l-jar fermenter containing 15 l of a medium having the same composition as the medium described above and cultured with aeration and stirring (300 rpm) at 30° C. for 4 days.

Thereafter, 15 l of the resultant culture liquor was filtered through a large Nutsche funnel using Radiolite #100 as a filtering aid to obtain about 15 l of culture filtrate. Ammonium sulfate was then added to the culture filtrate and the portion that precipitated with ammonium sulfate of 90% saturation was collected.

The yield of neuraminidase activity of the precipitate was about 80% and the specific activity was enhanced by about 5 times.

The precipitate was dissolved in a small amount (about 100 ml) of 0.01M tris-hydrochloric acid buffer (pH 7.0). The solution was then dialyzed against 10 l of the same buffer for 24 hours.

The dialysate was passed through a column of DEAE-Sephadex (1 l, diameter 6 cm) equilibrated with the same buffer. By this procedure, neuraminidase was adsorbed onto the DEAE-Sephadex. Impure proteins were washed out with the same buffer.

Elution was carried out using a concentration gradient solution of sodium chloride from 0.01M tris-hydrochloric acid buffer (pH 7.0) to the same buffer containing 1.0M sodium chloride. Active fractions eluted were combined and ammonium sulfate was added thereto. Portions precipitated with ammonium sulfate of 90% saturation were collected by centrifugation (12,000×g, 20 minutes) and dissolved in 10 ml of 0.01M tris-hydrochloric acid buffer (pH 7.0). The solution was dialyzed against 5 l of the same buffer for 24 hours.

After dialysis, the enzyme solution was passed through a column (500 ml, diameter 3.5 cm) of Sephadex G-75 equilibrated with the same buffer. The eluate was fractionally recovered, and fractions having high specific activity were collected and freeze-dried to obtain 50 mg of purified powdered neuraminidase preparation (specific activity 50 units/mg).

The purified enzyme had a specific activity elevated by about 2000 times as compared with the cell filtrate and the yield of the activity was about 50%.

EXAMPLE 2

In this example, the procedure of Example 1 was repeated except that the strain used was replaced by *Micromonospora globosa* NRRL B-2673 and the fermentation medium was replaced by a medium (pH 7.2) comprising 0.2 g/dl peptone, 0.1 g/dl meat extract, 0.1 g/dl enzyme extract and 2 g/dl mucin. Approximately 20 mg of purified neuraminidase having a 30 units/mg specific activity was obtained. The yield of the activity was about 30%.

EXAMPLE 3

In this example, the procedure of Example 1 was repeated except that the strain used was replaced by *Micromonospora chalcea* ATCC 12452. Approximately 30 mg of purified neuraminidase having a 40 units/mg specific activity was obtained. The yield of the activity was about 40%.

EXAMPLE 4

In this example, the quantitative determination of sialic acid in a sample is illustrated.

I. Composition of reagents (1) Enzyme reagent I:

| | |
|---|---|
| Neuraminidase (produced by *Micromonospora viridifaciens* ATCC 31146) | 200 units |
| 4-Aminoantipyrine | 60 mg |

The foregoing components were dissolved in 0.1M phosphate buffer (pH 6.0) to a total volume of 25 ml. Then, 2.5 ml portions of the liquid were poured into 10 ml-vial bottles followed by freeze-drying.

(2) Enzyme reagent II:

| | |
|---|---|
| NANA lyase | 300 units |
| Pyruvate oxidase | 500 units |
| Thiamine pyrophosphate | 50 mg |
| MgSO$_4$.7H$_2$O | 100 mg |
| Peroxidase | 1500 units |

The foregoing components were dissolved in 0.1M phosphate buffer (pH 6.0) to a total volume of 25 ml. Then, 2.5 ml portions of the liquid were poured into 10 ml-vial bottles by followed by freeze-drying.

(3) Color forming solution:

Phenol (300 mg) was dissolved in 0.1M phosphate buffer (pH 6.0) to total volume of 300 ml.

(4) Standard solution:

N-Acetylneuraminic acid (50 mg) was dissolved in 0.1M phosphate buffer (pH 6.0) to a total volume of 100 ml.

II. Procedure

The contents of a vial of enzyme reagent I and enzyme reagent II were dissolved in 30 ml of the color forming solution to make a reaction solution. Then, 3 ml of the reaction solution was taken out and 0.02 ml of serum (specimen) was added thereto. Incubation was carried out at 37° C. for 10 minutes. The absorbency of the reaction solution was measured at 500 nm. Separately, a calibration curve was prepared using the standard solution and a reagent blank. The test measurement results were compared to the calibration curve to determine the amount of sialic acid in the specimen. The result is shown in Table 1.

TABLE I

| Serum | Absorbency (500 nm) | Amount of sialic acid (mg/dl) |
|---|---|---|
| 1 | 0.185 | 47.5 |
| 2 | 0.225 | 57.0 |
| 3 | 0.205 | 52.2 |
| 4 | 0.255 | 64.1 |
| 5 | 0.210 | 53.0 |
| Standard | 0.200 | 50.0 |

What is claimed:

1. A process for producing neuraminidase which comprises culturing a neuraminidase producing microorganism belonging to the genus Micromonospora in a culture medium, accumulating neuraminidase in the culture liquor and thereafter recovering the neuraminidase therefrom.

2. A process according to claim 1, wherein said microorganism belongs to the species *Micromonospora viridifaciens, Micromonospora globosa* or *Micromonospora chalcea.*

3. A process according to claim 2, wherein said microorganism is *Micromonospora viridifaciens* ATCC 31146, *Micromonospora globosa* NRRL B-2673 or *Micromonospora chalcea* ATCC 12452.

4. A process according to claim 1, wherein said culturing step is carried out at 25° to 35° C. for 4 to 5 days at pH 6.0 to 7.0.

* * * * *